(12) United States Patent
Radl et al.

(10) Patent No.: US 10,849,707 B2
(45) Date of Patent: Dec. 1, 2020

(54) LAPAROSCOPIC MEASURING DEVICES AND METHODS OF LAPAROSCOPIC MEASURING

(71) Applicant: Boehringer Technologies, LP, Phoenixville, PA (US)

(72) Inventors: Christopher L. Radl, Malvern, PA (US); Steven C. Moulden, West Chester, PA (US)

(73) Assignee: Boehringer Technologies, LP, Phoenixville, PA (US)

( * ) Notice: Subject to any disclaimer, the term of this patent is extended or adjusted under 35 U.S.C. 154(b) by 373 days.

(21) Appl. No.: 15/954,777

(22) Filed: Apr. 17, 2018

(65) Prior Publication Data

US 2018/0353255 A1 Dec. 13, 2018

Related U.S. Application Data

(60) Provisional application No. 62/516,380, filed on Jun. 7, 2017.

(51) Int. Cl.
*A61B 90/00* (2016.01)
*A61B 17/00* (2006.01)

(52) U.S. Cl.
CPC ........ *A61B 90/06* (2016.02); *A61B 17/00234* (2013.01); *A61B 2090/061* (2016.02); *A61B 2090/062* (2016.02); *A61B 2090/0807* (2016.02)

(58) Field of Classification Search
CPC .............. A61B 90/06; A61B 2090/061; A61B 2090/0807; A61B 2090/0811
See application file for complete search history.

(56) References Cited

U.S. PATENT DOCUMENTS

| | | | |
|---|---|---|---|
| 4,726,121 A | 2/1988 | Ray et al. | |
| 9,427,318 B2 | 8/2016 | Hjelle et al. | |
| 2012/0203237 A1* | 8/2012 | Bryan | A61B 90/06 606/102 |
| 2012/0330323 A1* | 12/2012 | Lizardi | A61B 5/1076 606/102 |
| 2013/0206147 A1* | 8/2013 | Skalyni | A61F 6/16 128/836 |
| 2014/0066810 A1* | 3/2014 | Glazer | A61B 5/1076 600/587 |
| 2016/0270694 A1* | 9/2016 | Tang | A61B 5/1076 |

* cited by examiner

*Primary Examiner* — Daniel L Cerioni
*Assistant Examiner* — Raymond P Dulman
(74) *Attorney, Agent, or Firm* — Caesar Rivise, PC

(57) ABSTRACT

Laparoscopic instruments and methods of use are disclosed for measuring the distance between first and second portions of a target within a patient. The device includes a shaft, a ball, and a measuring member. The shaft has a distal end configured to extend into the patient. The ball is flexibly connected to the measuring member and configured for relative movement towards and away from the distal end of the shaft. The measuring member is slidable with respect to the shaft in response to relative movement between the ball and the distal end of the shaft and includes indicia thereon, whereupon a portion of the measuring member extends out of shaft so that the indicia provides an indication of the distance between the first and second portions of the target. One embodiment of the device is spring biased to automatically retract the ball after a measurement.

10 Claims, 5 Drawing Sheets

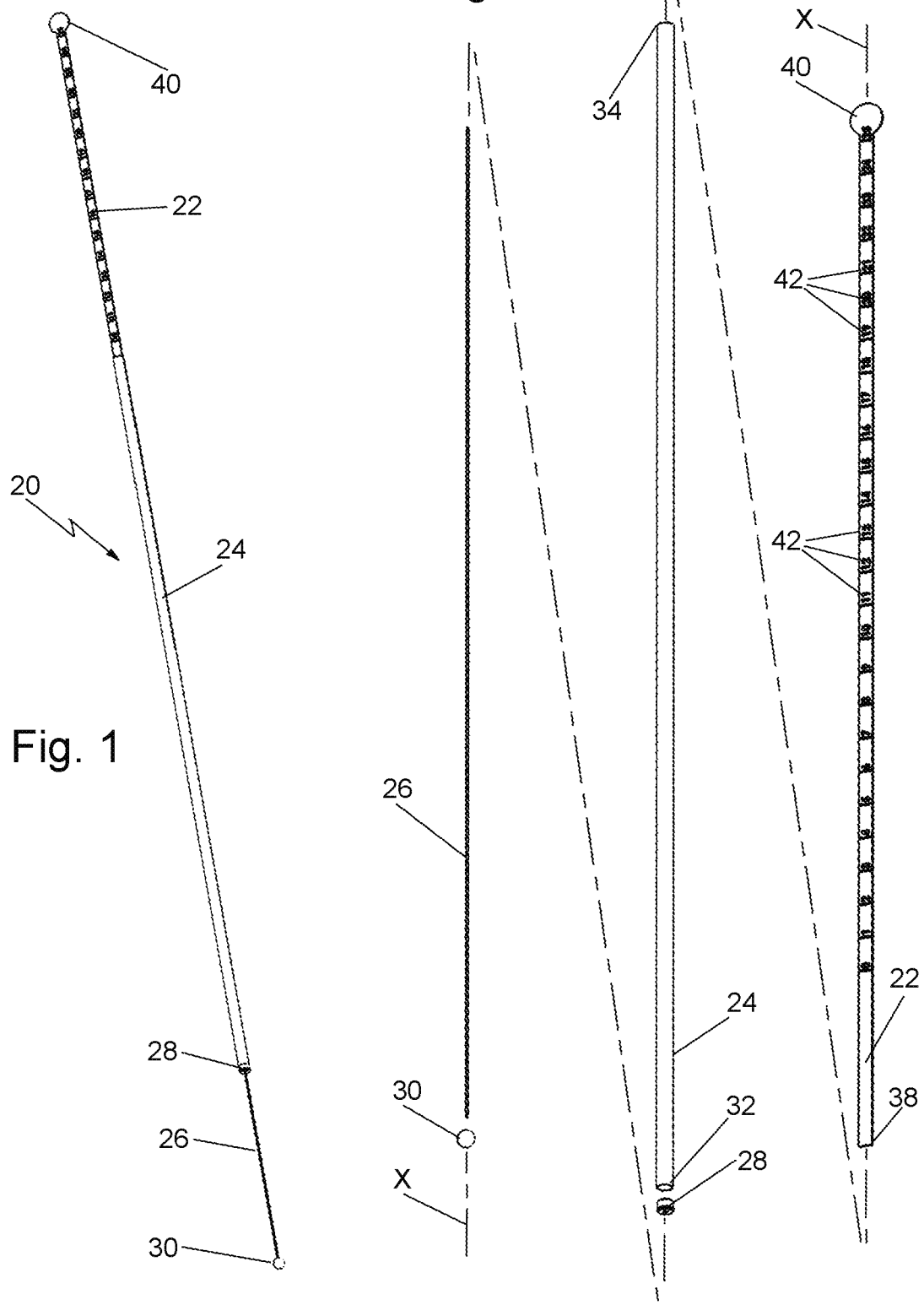

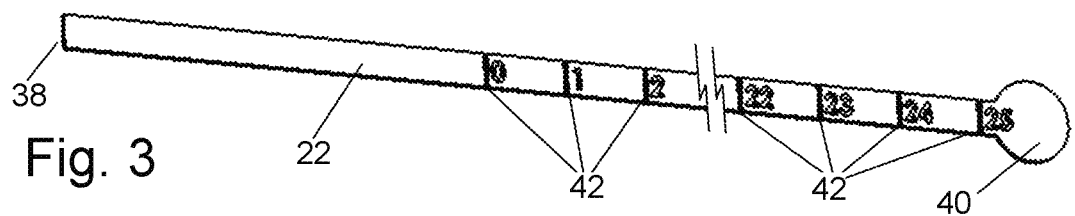
Fig. 3
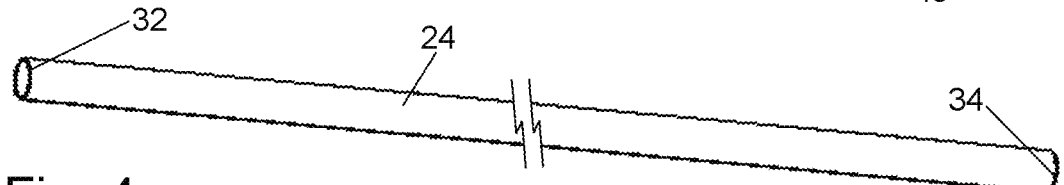
Fig. 4
Fig. 5 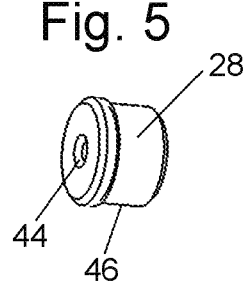 Fig. 6 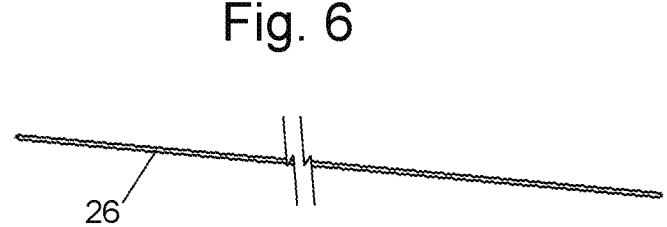 Fig. 7 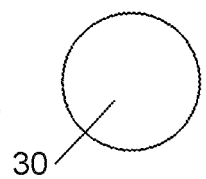
Fig. 8
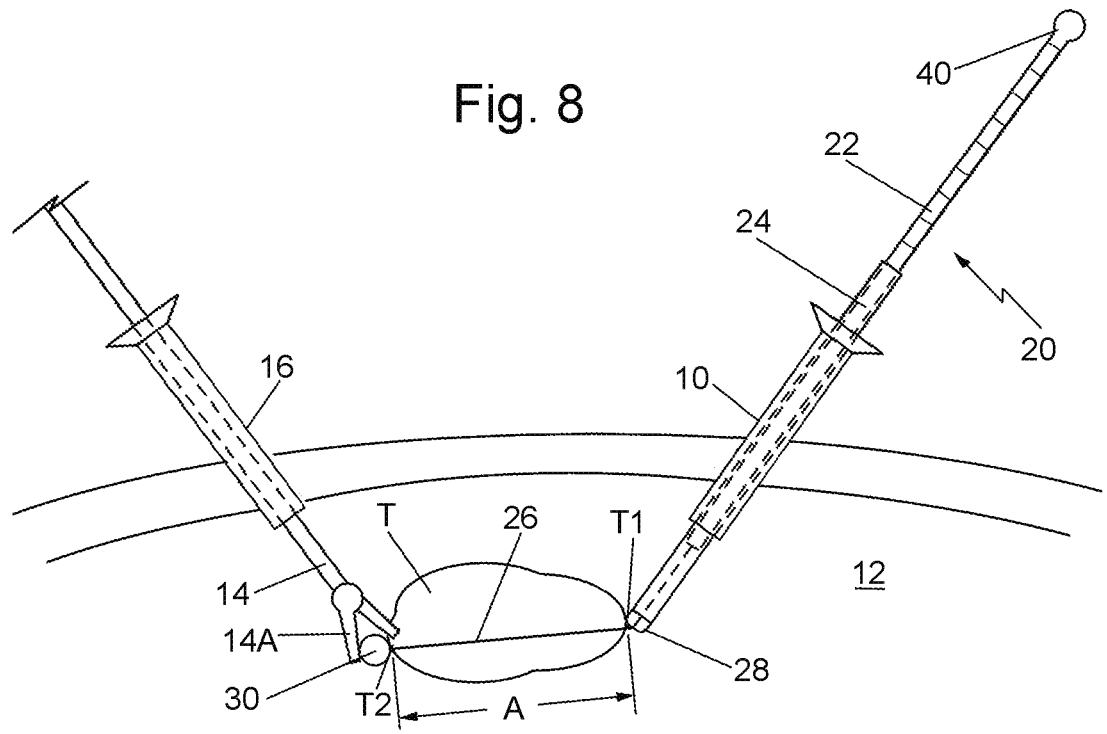

LAPAROSCOPIC MEASURING DEVICES AND METHODS OF LAPAROSCOPIC MEASURING

CROSS-REFERENCE TO RELATED APPLICATIONS

This utility application claims the benefit under 35 U.S.C. § 119(e) of Provisional Application Ser. No. 62/516,380 filed on Jun. 7, 2017, entitled Laparoscopic Measuring Devices and Methods of Laparoscopic Measuring. The entire disclosure of this provisional application is incorporated by reference herein.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISK

Not Applicable

FIELD OF THE INVENTION

The disclosed invention relates to medical devices and more particularly to laparoscopic devices for measuring a target within a patient, such as an organ, an internal feature of the patient, or an internal defect, and methods of measuring such targets laparoscopically.

BACKGROUND OF THE INVENTION

During some laparoscopic surgical procedures, such as the repair of a hernia, it is necessary to take a measurement of the hernia, so that an appropriately sized patch can be used to repair the defect. Heretofore such measurements have been made by using the jaws of a grasping instrument, the spacing of which jaws when opened being known. In particular the surgeon may insert the grasper into the insufflated peritoneal space and then use the grasper with its jaws open to measure the dimension of the hernia by counting the number of jaw spacings it takes to traverse the defect from one end of the defect to the other end of the defect. Other laparoscopic measurement approaches have entailed inserting one or more short lengths of a measuring tape into the insufflated peritoneal space and positioning the tape(s) next to the defect to determine its dimensions. Needless to say, these prior art approaches to laparoscopically measuring a target, be it tissue, an organ, or some internal feature or defect within the body of a patient, leaves much to be desired from the standpoint of accuracy, ease of measurement, etc. Thus, a need exists for a device or instrument which is simple in construction, low in cost, easy to use and which enables the effective laparoscopic measurement of internal targets within the body of a patient. The subject invention addresses those needs.

SUMMARY OF THE INVENTION

One aspect of this invention is a laparoscopic device for measuring a dimension of a target located within the body of a patient, the dimension being the distance between a first portion of the target and a second portion of the target. The device comprises an elongated shaft, an atraumatic body and an elongated measuring member. The elongated shaft has a distal end and a proximal end. The elongated shaft is configured to fit within a laparoscopic cannula or other port extending into the body of the patient, with the distal end of the elongated shaft located adjacent to the first portion of the target. The atraumatic body is coupled to the elongated shaft and is configured for relative movement towards and away from the distal end of the elongated shaft. The atraumatic body is configured to be located adjacent the second portion of the target. The elongated measuring member is coupled to the atraumatic body. The elongated measuring member includes indicia thereon and is configured to be slid with respect to the elongated shaft in response to relative movement between the atraumatic body and the distal end of the elongated shaft to cause a portion of the elongated measuring member to extend out of the proximal end of the elongated shaft, whereupon indicia located on the portion of the elongated measuring member provides an indication of the distance between the first and second portions of the target.

In accordance with one preferred aspect of the device of this invention, the elongated measuring member is flexibly coupled to the atraumatic body by a flexible filament connected between the atraumatic body and the elongated measuring member.

In accordance with another preferred aspect of the device of this invention, the elongated shaft is tubular and has a passageway extending from the distal end to the proximal end, with the elongated measuring member being disposed and slidable within the passageway.

In accordance with another preferred aspect of the device of this invention, the elongated measuring member comprises a stop configured to prevent the elongated measuring member being pulled out of the distal end of the elongated shaft.

In accordance with another preferred aspect of the device of this invention, the device additionally comprises a bushing located at the distal end of the elongated tubular shaft. The busing includes an opening through which the flexible filament extends.

In accordance with another preferred aspect of the device of this invention the atraumatic body is a ball.

In accordance with another preferred aspect of the device of this invention the elongated measuring member includes a proximal end configured to be grasped by a user to extend the proximal end of the elongated measuring member to a maximum distance from the proximal end of the elongated tubular shaft, whereupon the atraumatic body is located immediately adjacent the distal end of the elongated tubular shaft.

In accordance with another preferred aspect of the device of this invention the elongated measuring member comprises a scale having regularly spaced marks extending along a portion of the elongated measuring member.

In accordance with another preferred aspect of the device of this invention the elongated measuring member is resiliently-loaded to retract the atraumatic body to a position adjacent the free end of the elongated shaft.

In accordance with another preferred aspect of the device of this invention the device additionally comprises an elongated resilient tension member connected between the distal end portion of the elongated tubular shaft and a portion of the elongated measuring member.

In accordance with another preferred aspect of the device of this invention the elongated resilient tension member comprises a tension spring.

In accordance with another preferred aspect of the device of this invention the elongated measuring member is flexibly coupled to said atraumatic body by a flexible filament connected between the atraumatic body and a distal portion of the elongated measuring member, and wherein the device additionally comprises a pulley located adjacent the proximal end of the elongated shaft, with a portion of the filament extending around the pulley.

Another aspect of this invention is for measuring a first dimension of a target located within the body of a patient, with the first dimension of the target being the distance between a first portion of the target and a second portion of the target. The method entails providing a measuring device comprising an elongated shaft, an atraumatic body and an elongated measuring member. The elongated measuring member has indicia thereon. The elongated shaft has a distal end and a proximal end. The device is introduced into the body of the patient through a laparoscopic cannula or other port, whereby the distal end of the elongated shaft is located at a first position adjacent the first portion of the target. The atraumatic body is located at a second position adjacent the second portion of the target. The positioning of the distal end of the elongated shaft at the first position and the positioning of the atraumatic body at the second position results in relative movement between the atraumatic body and the distal end of the elongated shaft, whereupon a portion of the elongated measuring member extends out of the proximal end of the elongated shaft such that indicia located on the portion of the elongated measuring member is perceptible from outside the body of the patient to provide an indication of the first dimension.

In accordance with one preferred aspect of the method of this invention, the distal end of the elongated shaft is held at the first position and the atraumatic body is moved to the second position while the distal end of the elongated shaft is held at the first position.

In accordance with another preferred aspect of the method of this invention, the moving of the atraumatic body is accomplished by an instrument extended into the body of the patient adjacent the target.

In accordance with another preferred aspect of the method of this invention, the target is located within an insufflated abdomen of the patient.

In accordance with another preferred aspect of the method of this invention, the target comprises an organ, or an internal feature of the patient, or an internal defect of the patient.

In accordance with another preferred aspect of the method of this invention, the method comprises measuring a second dimension of the target after measuring the first dimension of the target.

In accordance with another preferred aspect of the method of this invention, the measuring the second dimension of the target comprises moving at least one of the distal end portion of the elongated shaft and the atraumatic body to a position adjacent a third portion of the target.

In accordance with another preferred aspect of the method of this invention, the measuring of the second dimension of the target comprises moving the distal end portion of the elongated shaft to a third position adjacent a third portion of the target, holding the distal end portion in position thereat and moving the atraumatic body to a fourth position adjacent a fourth portion of the target. That action causes a portion of the elongated measuring member to extend out of the proximal end of the elongated shaft, whereupon indicia located on the portion of the elongated measuring member is perceptible from outside the body of the patient to provide an indication of the distance between the third and fourth portions of the target. The distance separating the third and fourth portions of the target is the second dimension of the target.

In accordance with another preferred aspect of the method of this invention, the measuring of the second dimension of the target comprises holding the distal end portion of the elongated tubular shaft at the first position, moving the atraumatic body to a third position adjacent a third portion of the target. That action causes a portion of the elongated measuring member to extend out of the proximal end of the elongated tubular shaft, whereupon indicia located on the portion of the elongated measuring member is perceptible from outside the body of the patient to provide an indication of the distance between the first and third portions of the target. The distance separating the first and third portions of the target is the second dimension of the target.

In accordance with another preferred aspect of the method of this invention, the measuring of the second dimension of the target comprises holding the atraumatic body at the second position, moving the distal end of the elongated shaft to a third position adjacent a third portion of the target. That action causes a portion of the elongated measuring member to extend out of the proximal end of the elongated tubular shaft, whereupon indicia located on the portion of the elongated measuring member is perceptible from outside the body of the patient to provide an indication of the distance between the second and third portions of the target. The distance separating the second and third portions of the target is the second dimension of the target.

BRIEF DESCRIPTION OF THE DRAWING FIGURES

FIG. 1 is an isometric view of one exemplary embodiment of a manually retractable laparoscopic measuring instrument or device constructed in accordance with this invention;

FIG. 2 is a slightly enlarged exploded isometric view of the manually retractable laparoscopic measuring device shown in FIG. 1;

FIG. 3 is an enlarged isometric view of a measuring tape forming one component of the manually retractable laparoscopic measuring device shown in FIG. 1;

FIG. 4 is an enlarged isometric view of an elongated shaft forming another component of the manually retractable laparoscopic measuring device shown in FIG. 1;

FIG. 5 is an enlarged isometric view of a nose bushing forming another component of the manually retractable laparoscopic measuring device shown in FIG. 1;

FIG. 6 is an enlarged isometric view of a filament or string forming another component of the manually retractable laparoscopic measuring device shown in FIG. 1;

FIG. 7 is an enlarged isometric view of a ball forming another component of the manually retractable laparoscopic measuring device shown in FIG. 1;

FIG. 8 is an illustration of the use of the manually retractable laparoscopic measuring device shown in FIG. 1 to laparoscopically measure a first dimension "A" of an anatomic structure within the abdomen of a patient, with the first dimension "A" being the distance between first and second portions of the target;

DETAILED DESCRIPTION OF THE PREFERRED EMBODIMENTS

Figure 9:
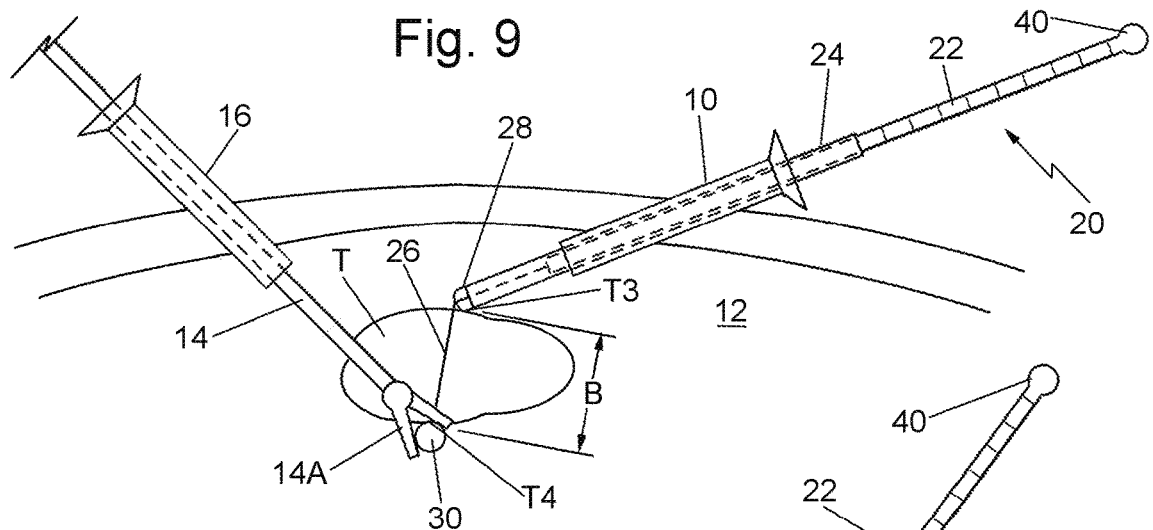
FIG. 9 is an illustration, similar to FIG. 8, but showing the use of the manually retractable laparoscopic measuring device to measure a second dimension "B" of the anatomic structure shown in FIG. 8, but with the second dimension "B" being the distance between third and fourth portions of the target.

Referring now to the drawings wherein like characters refer to like parts there is shown at 20 in FIG. 1 one exemplary embodiment of a manually retractable laparoscopic device for measuring an anatomic target, e.g., tissue, an organ, some other anatomic structure or defect, within the body of a patient. The device 20 is in the form of an elongated instrument configured for laparoscopic insertion into the body of a patient to the site of the anatomic target T to be measured.

The device 20 basically comprises an elongated measuring member 22, an elongated shaft 24, a filament or string 26, a nose bushing 28 and a rounded or otherwise atraumatically shaped body 30. The elongated shaft 24 is best seen in FIGS. 1, 2 and 4, and is preferably a linear tubular body that includes a distal end 32, a proximal end 34 and a central passageway 36 extending along a longitudinal axis X of the device between the distal end 32 and the proximal end 34. The shaft is open at its proximal end to enable a portion of the elongated measuring member to extend out of it, as will be described later. The nose bushing 28 is located within the distal end of the tubular shaft, as will also be described later. The tubular shaft 24 is of small external diameter, e.g., 5 mm, to enable it to be introduced into the patient's body through a conventional trocar or other port. The tubular shaft 24 can be formed of any suitable, biocompatible material, e.g., a 304 stainless steel seamless thin walled tube. It should be pointed out at this juncture that the 5 mm external diameter is merely exemplary. Thus, the tubular shaft 24 may be of lesser or greater diameter, depending on the application of the device 20.

The elongated measuring member 22 is best seen in FIGS. 1-3 and basically comprises an elongated thin linear strip or tape having a distal end 38 and a proximal end 40. The proximal end 40 is in the form of an enlarged tab. A portion of the measuring member 22 from the tab 40 to a point near the distal end 38 includes indicia 42 therealong. The indicia form a ruler or scale of equidistantly spaced lines, with numbers adjacent the lines indicating the distance in centimeters, measured from the line designated as "0" which is located closest to the distal end 38 of the member 22. In the exemplary embodiment of FIG. 1 there are twenty-six lines with associated sequential numbers from 0 to 25 designating successive centimeter measurements from the '0' line of the scale. The line designated by "25" is located immediately adjacent the tab 40. As will be described later, when the device 20 is being used to measure a target within the body of the patient the proximal end of the measuring member will extended out of the open proximal end of the tubular shaft, such that the particular indicium of the indicia 42 that is located immediately adjacent the open distal end of the tubular shaft will provide an indication of the dimension measured. The measuring tape 22 can be formed of any suitable biocompatible material, e.g., plastic, stainless steel, etc.

It should be noted at this juncture that while the exemplary embodiment of the measuring indicia 42 is in the form of a ruler or scale of equidistantly spaced lines and associated numbers that is merely exemplary. Thus, the measuring indicia 42 can take various other forms, e.g., sequentially different colors, etc., so long as it a can be perceived from outside the body of the patient when the device is in use and which will provide the user with visual information that the user can visually perceive to determine the dimension(s) of the target.

The measuring tape 22 is configured to fit and slide within the passageway 36 of the tubular shaft 24. To that end, the width of the measuring tape is just slightly less than the inner diameter of the passageway 36 of the tubular shaft 24. The measuring tape is disposed within the passageway 36 so that its distal end 38 is located within the passageway, with its tab 40 located outside of the open proximal end 34 of the tubular shaft 24. The tab 40 is of greater diameter than the inner diameter of the passageway 36 and forms a stop for engagement with the proximal end of the tubular shaft. The distal end of the measuring tape is fixedly secured to one end of the filament or string 26.

The filament or string 26 is best seen in FIGS. 1, 2 and 6 and is formed of any suitable flexible material, such as braided suture material, monofilament, etc. The filament or string has a distal end and a proximal end. The proximal end of the filament is fixedly connected to the distal end of the measuring tape 22, while the distal end of the filament is fixedly connected to the atraumatic body 30.

As best seen in FIGS. 1, 2 and 7 the atraumatic body 30 is in the form of a small diameter, ball. The ball is preferably of the same diameter or slightly smaller than the diameter of the tubular shaft 24, e.g., 5 mm and is formed of any suitable biocompatible material, e.g., plastic, stainless steel, etc. It should be point out at this junctures that the ball is merely one exemplary embodiment of various atraumatically shaped bodies that can be used in the device 20. What is important is that the atraumatic body is suitable to be grasped by the jaws of a conventional laparoscopic grasper or some other laparoscopically inserted instrument to hold it in position adjacent a portion of the target to be measured (as will be described later), and is not sharp (e.g., is rounded). As such, the atraumatically shaped body 30 does not present a hazard to internal structures within the patient's body.

As mentioned earlier the nose bushing 28 is located within the distal end 32 of the tubular shaft 24. The nose bushing is best seen in FIGS. 1, 2 and 5, and basically comprises a short cylindrical body having a small diameter passageway 44 centered on the longitudinal axis X, and an outer annular recess 46. The annular recess 46 is configured to receive the inner surface of the distal end 32 of the tubular shaft to fixedly secure the nose bushing therein. The internal diameter of the passageway of the nose bushing 44 is just slightly larger than the outside diameter of the filament 26. The atraumatically shaped body 30 is located outside of the distal end of the nose bushing 28, with the filament or string 26 extending through the passageway 44 in the nose busing into the central passageway 36 of the tubular shaft 24 to the point where it is connected to the distal end 38 of the measuring tape 22. The entryway 46 to the passageway 44 of the nose bushing is in the form of a rounded chamfer to ensure that the filament isn't cut or otherwise damaged upon its extension and retraction through the bushing during use of the device. The nose bushing can be formed of any suitable material, e.g., plastic or stainless steel.

Use of the device 20 is as follows. When the device is in its normal or retracted state and ready for use, the measuring tape 22 is retracted or pulled in the proximal direction so that the atraumatically shaped body or ball 30 is in engagement or located immediately adjacent the nose bushing at the distal end of the tubular shaft 24. At that time the measuring tape 22 will be in its normal fully retracted position, whereupon a major portion of the measuring tape will extend out of the proximal end 34 of the tubular shaft 24. At that position the ruler or scale line and its associated numerical indicium "0" of the indicia 42 will be located immediately adjacent the proximal end 34 of the tubular shaft. The distal end of the device 20 can then be inserted into the patient's body to a position adjacent the target to be measured. For example, as shown in FIG. 8, the device 20 is inserted through a conventional trocar 10 extending into an insufflated peritoneal space 12 in a patient, so that the nose bushing 28 is in engagement or located immediately adjacent a first portion T1 of a target T to be measured. The atraumatically shaped body or ball 30 is then grasped by the jaws 14A of a conventional grasper 14, which extends through another trocar 16 into the peritoneal space 12. The grasper is then used to pull the ball from immediately adjacent the nose bushing to another position wherein the ball is in engagement or located immediately adjacent a second portion T2 of the target T and held thereat. That action has the effect of dragging on the filament 26 in the distal direction, which in turn pulls the measuring tape 22 in the distal direction from its fully extended position to an extended measuring position, whereupon the indicia 42 indicates the distance that the ball has been pulled. For example if the ball 30 is pulled four centimeters from the portion T1 of the target to the portion T2 of the target, as shown in FIG. 8, that will pull the measuring tape 22 four centimeters in a distal direction from its full extended state, whereupon the ruler or scale line with the numerical indicium "4" will be located immediately adjacent the open proximal end 34 of the tubular shaft, so that the user will know that the dimension "A" of the target between portions T1 and T2 is four centimeters.

If another dimension of the target T is to be measured, the user can reset the device 20 by pulling on the tab 40 of the measuring tape in the proximal direction until it is in its normal fully retracted position. In the fully retracted position the ball 30 will again be located immediately adjacent the nose bushing 28. The device 20 can then be moved and oriented, like shown in FIG. 9, so that the nose bushing 28 is in engagement or located immediately adjacent a third portion T3 of a target T to be measured. The atraumatically shaped body or ball 30 is then grasped by the jaws 14A of the grasper 14 to pull the ball 30 from immediately adjacent the nose bushing to a position wherein the ball is in engagement or located immediately adjacent a fourth portion T4 of the target T and held thereat. That action has the effect of dragging on the filament 26 in the distal direction, which in turn pulls the measuring tape 22 in the distal direction from its fully extended position to an extended measuring position, whereupon the indicia 42 indicates the distance that the ball has been pulled. For example if the ball 30 is pulled two centimeters from the portion T3 of the target to the portion T4 of the target, as shown in FIG. 9, that will pull the measuring tape 22 two centimeters in a distal direction from its full extended state, whereupon the ruler or scale line with the numerical indicium "2" will be located immediately adjacent the open proximal end 34 of the tubular shaft. Thus, the user will know that the dimension "B" of the target between portions T3 and T4 is two centimeters.

Figure 10:
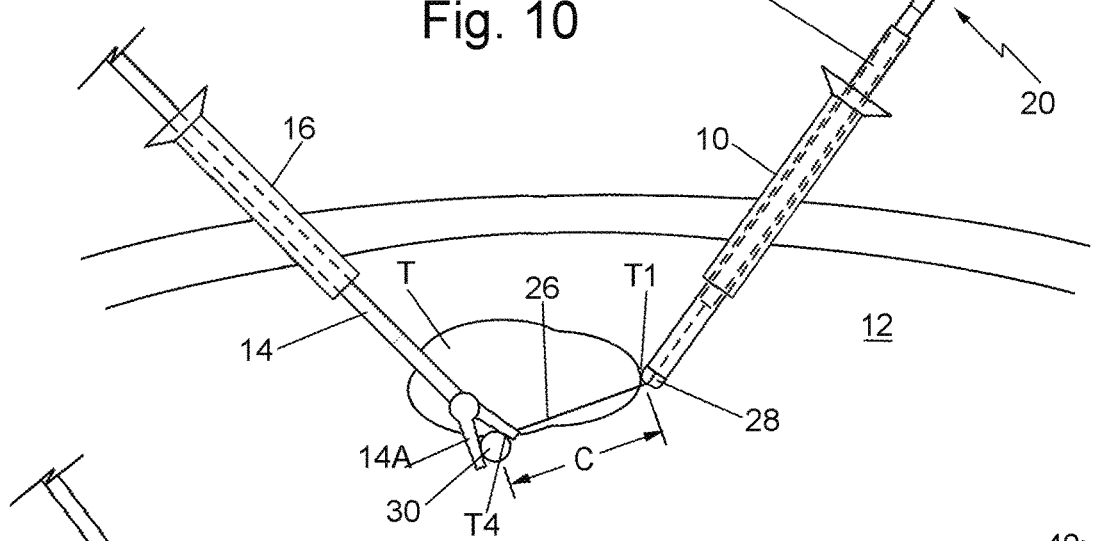
FIG. 10 is an illustration, similar to FIG. 8, but showing the use of the manually retractable laparoscopic measuring device to measure a second and different dimension "C" of an anatomic structure shown in FIG. 8, but with the second dimension "C" being the distance between the first portion of the target shown in FIG. 8 and the fourth portion of the target shown in FIG. 9.

It should be noted that while the above described methods for measuring dimensions of the target has involved holding the device 20 with its nose bushing 28 in a fixed position with respect to one portion of the target T and pulling or otherwise moving the atraumatically shaped body 30 to another portion of the target, that is not the only way the device can be used to measure a dimension of a target. Thus, as long as at least one of the nose bushing 28 and the atraumatically shaped body is moved relative to the other so that the filament 26 will be extended out of the device to cause concomitant movement of the measuring tape 22, the device can be used to measure any dimension of an internal target. For example, with the device in its normal retracted state the ball 30 can be grasped by the jaws 14A of the grasper 14 to hold the ball 30 in a position immediately adjacent the portion T4 of the target, as shown in FIG. 10. The device 20 can then be moved so that the nose bushing 28 will be in engagement or immediately adjacent the portion T1 of the target. The relative movement between the ball 20 and the nose bushing 28 has the effect of dragging on the filament 26 in the distal direction, which in turn pulls the measuring tape 22 in the distal direction from its fully extended position to an extended measuring position. Thus, for example, if the moving of the nose bushing to the position T1 while the ball is held in position T4 results in the spacing between the ball 30 and the nose bushing 28 of three centimeters, that will pull the measuring tape 22 three centimeters in a distal direction from its full extended state, whereupon the ruler or scale line with the numerical indicium "3" will be located immediately adjacent the open proximal end 34 of the tubular shaft. Thus, the user will know that the dimension "C" of the target between portions T1 and T4 is three centimeters.

Figure 11:
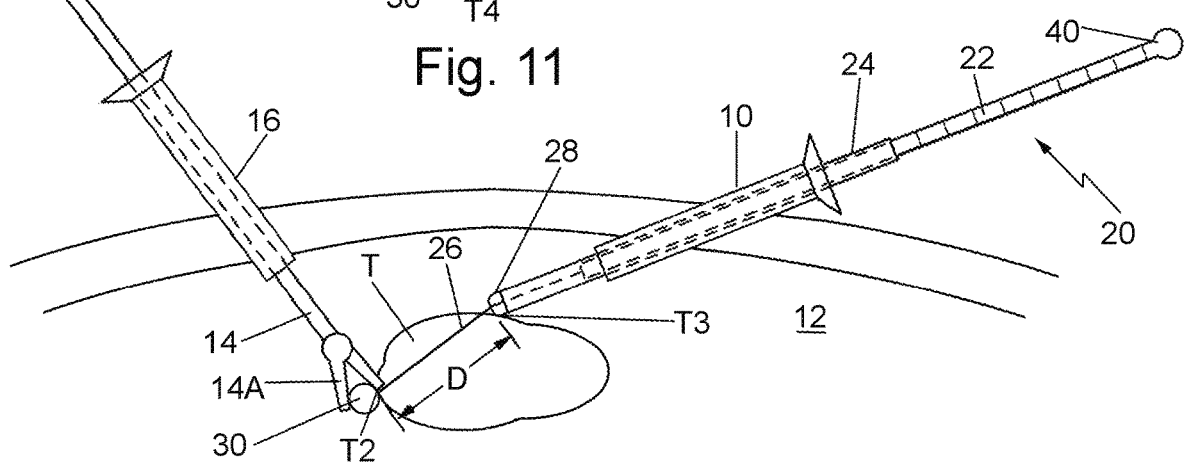
FIG. 11 is an illustration, similar to FIG. 8, but showing the use of the manually retractable laparoscopic measuring device to measure a second and still other different dimension "D" of an anatomic structure shown in FIG. 8, but with the second dimension "D" being the distance between the third portion of the target shown in FIG. 9 and the second portion of the target shown in FIG. 8.

FIG. 11 shows another measurement of the target T. In this case the dimension D between portions T2 and T3 of the target is measured. Thus, in this example with the device in its normal fully retracted state the ball 30 can be grasped by the jaws 14A of the grasper 14 to hold the ball 30 in a position immediately adjacent the portion T2 of the target. The device 20 can then be moved so that the nose bushing 28 will be in engagement or immediately adjacent the portion T3 of the target. The relative movement between the ball 30 and the nose bushing 28 has the effect of dragging on the filament 26 in the distal direction, which in turn pulls the measuring tape 22 in the distal direction from its fully extended position to an extended measuring position. Thus, for example, if the moving of the nose bushing to the position T3 while the ball is held in position T2 results in the spacing between the ball 30 and the nose bushing 28 of three centimeters, that will pull the measuring tape 22 three centimeters in a distal direction from its full extended state, whereupon the line with the indicium "3" will be located immediately adjacent the open proximal end 34 of the tubular shaft. As such, the user will know that the dimension "D" of the target between portions T2 and T3 is three centimeters.

As should be appreciated by those skilled in the art since the filament or string is flexible the atraumatically shaped body to which it is secured can be pulled in any direction with respect the longitudinal axis X. Moreover, the filament is sufficiently long, e.g., 30.5 cm, to reach any portion of the target, irrespective of the size or shape of the target and the location of that portion of the target.

Figure 12:
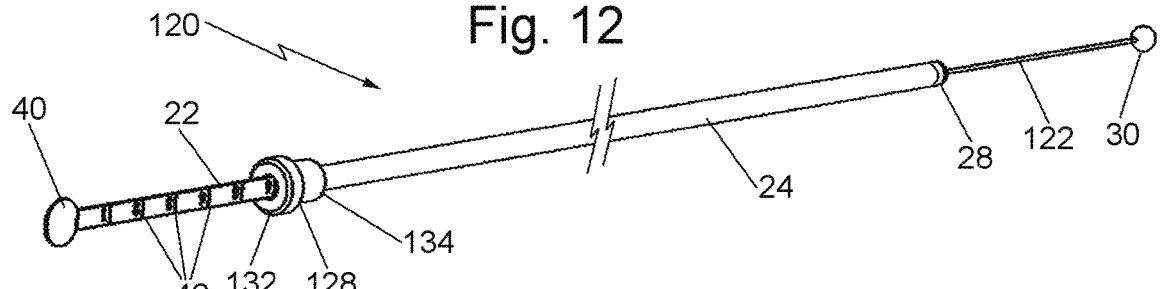
FIG. 12 is an isometric view of one exemplary embodiment of an automatically retractable laparoscopic measuring device constructed in accordance with this invention.

Turning now to FIG. 12, there is shown an alternative retractable laparoscopic device 120 for measuring the anatomic target T or any other tissue, organ, or other structures or defect within the body of a patient. The device 120 is similar in many respects to the device 20, except for the fact that it is automatically retractable, i.e., the measuring member will automatically retract to its normal fully retracted state when the atraumatically shaped member 30 is released or free. In the interest of brevity the components of the device 120 which are common to the device 20 will be given the same reference numbers and the details of their construction and operation will not be reiterated.

Figure 13:
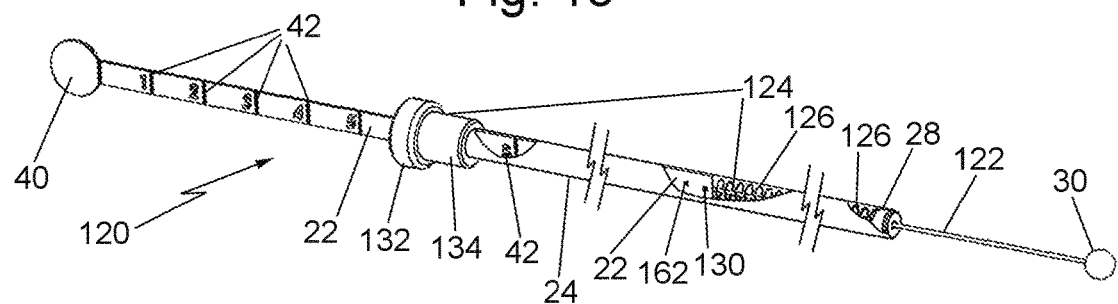
FIG. 13 is a slightly enlarged isometric view of the automatically retractable laparoscopic measuring device of FIG. 12, with portions broken away to show internal details of the device.
Figure 14:
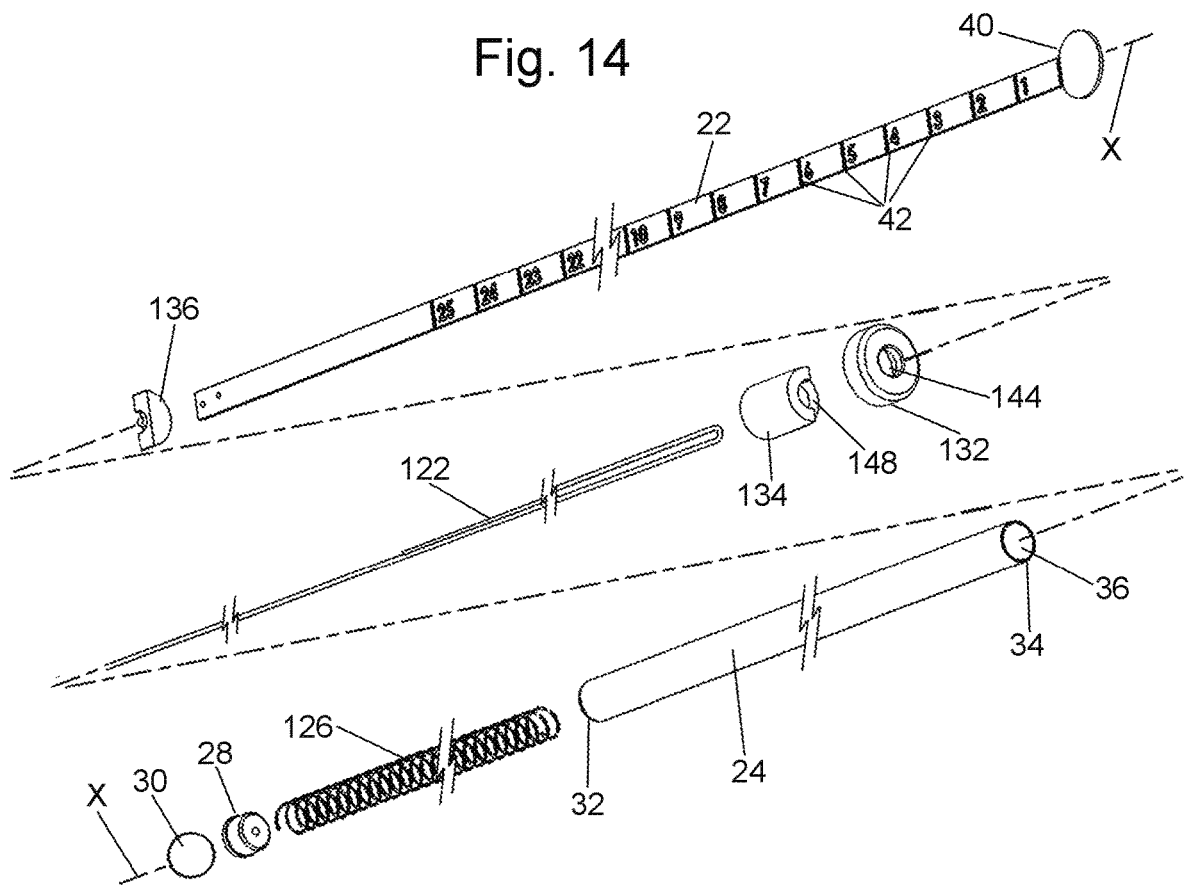
FIG. 14 is an enlarged exploded isometric view of the automatically retractable laparoscopic device shown in FIG. 12.

As can be seen in FIGS. 12-14 the automatically retractable laparoscopic measuring device 120 basically comprises an elongated measuring member 22, an elongated shaft 24, a filament or string 122, a nose bushing 28, a rounded or otherwise atraumatically shaped body 30, and a spring-loaded automatic retraction assembly 124. The measuring member includes the heretofore identified indicia 42 thereon, except that the line designated as "0" is located closest to the proximal end tab 40 of the member 22. In the exemplary embodiment of FIG. 12 there are twenty-six lines with associated sequential numbers from 0 to 25 designating successive inch measurements from the '0" line of the scale, with the line designated by "25" being located towards the distal end of the measuring member for reasons that will become apparent later.

Figure 17:
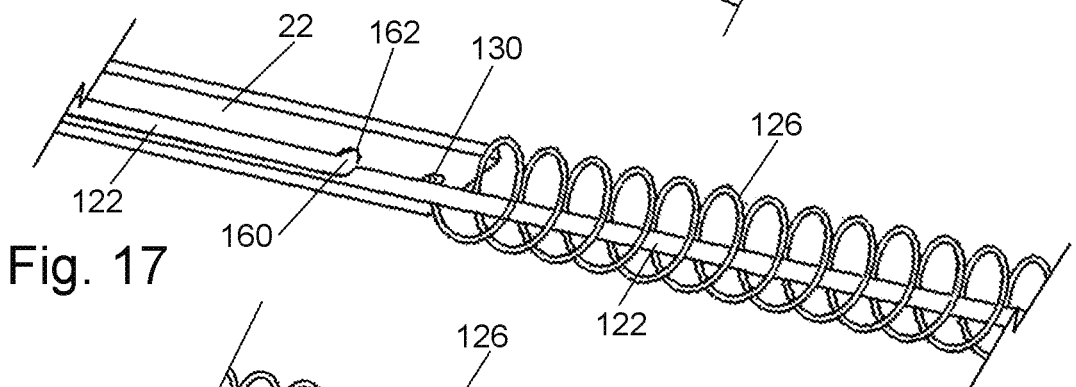
FIG. 17 is an enlarged isometric view of some of the components, i.e., the measuring tape, the filament, and the retraction spring, of the automatically retractable laparoscopic device shown in FIG. 12.
Figure 18:
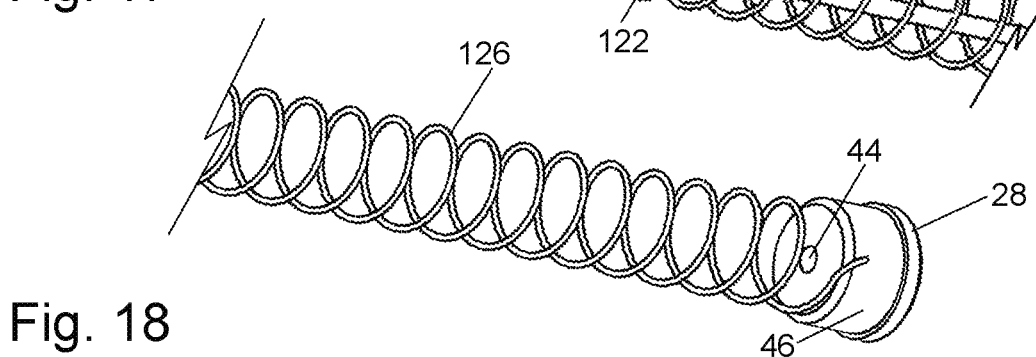
FIG. 18 is an enlarged isometric view of some of the components, i.e., the retraction spring and nose bushing, of the automatically retractable laparoscopic device shown in FIG. 12.

The spring-loaded automatic retraction assembly 124 basically comprises a resilient tension-applying member 126 (FIGS. 13, 14, 17 and 18) and an anchor subassembly 128 (FIGS. 12-15). In the exemplary embodiment 120 shown, the resilient tension-applying member 126 is in the form of a helical tension spring. However, it is contemplated that other resilient tension applying members, e.g., an elastic strip or tape, can be used in lieu of the spring. In any case the resilient tension applying member includes a distal end which is fixedly secured to distal end 32 of the tubular shaft 24. In the exemplary embodiment shown the distal end of the spring 136 is trapped between the inner surface of the passageway 36 at the distal end 32 of the tubular shaft 24 and the peripheral outer surface of the nose bushing 28. The distal end of the spring may be directly connected to the nose bushing itself by any suitable means, if desired. The proximal end of the spring is connected to the distal end of the measuring member. In particular, as best seen in FIG. 17 the distal end of the measuring tape includes an aperture 130 into which the proximal end of the spring extends.

Figure 15:
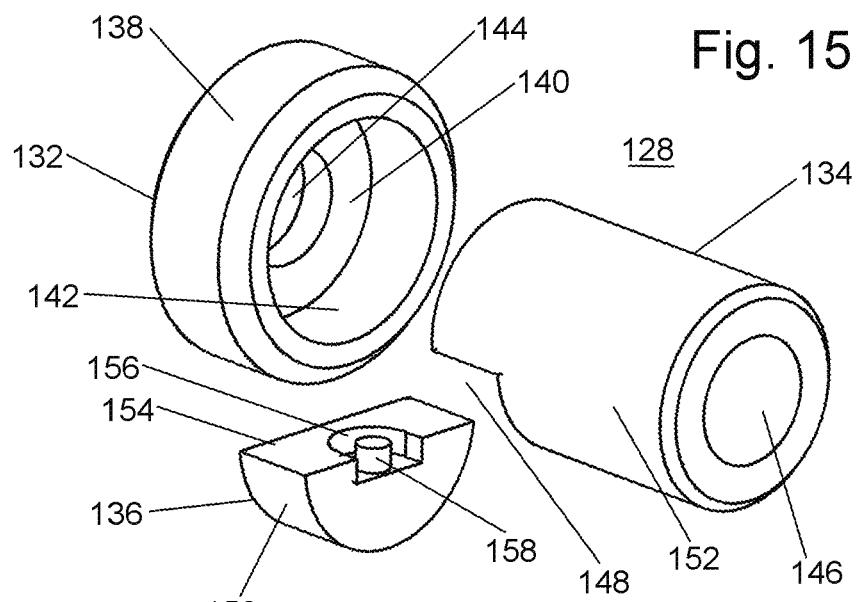
FIG. 15 is an even more enlarged exploded isometric view of some of the components, i.e., a cap, a guide sleeve, and a guide insert, of the automatically retractable laparoscopic device shown in FIG. 12.

The anchor subassembly 128 is located at the proximal end 34 of the tubular shaft 24. As best seen in FIG. 15 the anchor subassembly comprises a cap 132, a guide sleeve 134 and a guide insert 136. The cap 132 is a cylindrical body having a cylindrical sidewall 138, an end wall 140, and a circular cavity 142 bounded by the sidewall 138 and end wall 140. The end wall 138 includes a central hole 144. The circular cavity 142 is configured to receive the proximal end 34 of the tubular shaft. To that end, the inner diameter of the circular cavity is slightly greater than the outer diameter of the proximal end of the tubular shaft. The central hole 144 is configured so that the measuring member or tape 22 can extend therethrough, as will be described later.

The guide sleeve is a cylindrical body that includes a central passageway 146 extending its entire length. The proximal end of the guide sleeve includes a semi-circular notch 148. The notch 148 is configured to receive the guide insert 136. To that end, the guide insert 136 is shaped to mate with the guide sleeve 134 when the guide insert is located in the notch 148, such that the arcuate outer surface 150 of the guide insert is flush with the circular outer surface 152 of the guide sleeve 134. The guide insert 138 includes a generally planar upper surface 154 in which a U-shaped channel 156 is located. The U-shaped channel includes a pin 158 projecting upward between the legs of the channel, with the top surface of the pin 158 being flush with the upper surface 154 of the guide insert. The pin 158 serves as a pulley about which the filament or string 122 extends.

Figure 16:
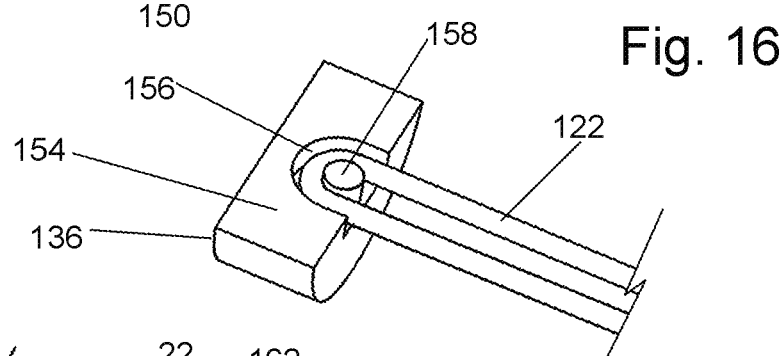
FIG. 16 is an enlarged isometric view of some of the components, i.e., the guide insert and the filament, of the automatically retractable laparoscopic device shown in FIG. 12.

The filament or string 122 is an elongate flexible member formed of any suitable material, e.g., monofilament, or braided suture, stainless steel flexible cable, etc. The distal end of the filament or string is fixedly secured to the atraumatically shaped body or ball 30. The opposite end 160 of the filament is fixedly secured to the distal end of the measuring tape 22. In particular, as can be seen in FIG. 17, the filament end 160 extends into and is secured within an aperture 162 in the distal end of the measuring tape. As best seen in FIG. 16, the portion of the filament or string 122 located between the atraumatically shaped body or ball 30 and the filament end 160 extends through the channel 156 and around the pulley or pin 158.

The guide insert 138 with the filament portion located in its channel 156 and about its pin 158 is located within the notch 148 of the guide sleeve to form an integral guide member. The guide member is configured to tightly fit and be anchored in place within the proximal end portion of the central passageway 36 of the tubular shaft 24, with the cap 132 closing off that end portion. Accordingly, the pulley 158 will be fixedly secured at the proximal end of the tubular shaft 24. As such, the portion of the filament 122 which is connected to the distal end of the measuring tape and the portion of the filament that is connected to the atraumatically shaped body 30 extend from the fixedly located pulley 158 through the central passageway 146 of the guide sleeve to their respective connection points. The measuring tape 22 also extends through the passageway 146 in the guide sleeve 134 and the central opening 144 in the cap 132.

The operation of the automatic retraction assembly 124 is as follows. If the ball is free, i.e., not held in place by a grasper or any other instrument or body, the tension spring 126, which is connected to the distal end of the tubular shaft 24, automatically applies tension to the distal end of the measuring tape 22. That action pulls the measuring tape 22 in the distal direction through the central passageway 36 towards the nose bushing 28. The movement of the measuring tape in the distal direction causes the filament portion that is connected to its distal end and which is located on one side of the pulley to move in the distal direction. Accordingly, the portion of the filament to which the ball 30 is connected (and which is located on the opposite side of the pulley) moves in the proximal direction retracting the ball to its normal or fully retracted position. When the ball is in its normal or fully retracted position, the measuring tape 30 will be retracted to its maximum position inside the proximal end of the tubular shaft. In that position the ruler or scale line and the numerical indicium "0" of the indicia 42 on the measuring tape will be aligned with the proximal end 34 of the tubular shaft, thereby indicating that the ball is 0 centimeters from the nose bushing 28. In that state the device 120 is ready for use. The use of the device 120 can be the same as that described with reference to the device 20, except that after a measurement has been completed and either the ball released from its position adjacent a portion of the target or the nose bushing released from its position adjacent a portion of the target, the automatic retraction assembly will automatically retract the filament, ball and measuring tape to the normal or fully retracted position.

It should be pointed out at this juncture that the device 20 as described above is merely exemplary of various components and arrangements that can be used to achieve the ends of this invention. Thus other devices can be constructed in accordance with the teaching of this invention. For example, if some mechanism is desired to retract the ball, filament and measuring tape in lieu of accomplishing that manually (like the device 20) or automatically (like the device 120), the device may include a detent mechanism to enable the ball, filament and tape to be in any position until the detent mechanism is actuated, whereupon the ball, filament and tape will be moved to the normal fully retracted position.

Without further elaboration the foregoing will so fully illustrate our invention that others may, by applying current or future knowledge, adopt the same for use under various conditions of service.

We claim:

1. A laparoscopic device for measuring a dimension of a target located within the body of a patient, the dimension being the distance between a first portion of the target and a second portion of the target, said device comprising:
   an elongated tubular shaft having a distal end, a proximal end and a central linear passageway having a central longitudinal axis extending therethrough from said distal end to said proximal end, said elongated tubular shaft being configured to fit within a laparoscopic cannula extending into the body of the patient, with the distal end of said elongated shaft located adjacent the first portion of the target;
   a flexible filament extending through a portion of said central passageway;
   an atraumatic body coupled to said flexible filament and configured for relative movement between a retracted position immediately adjacent said distal end of said elongated shaft and an extended position remote from said distal end of said elongated shaft, and vice versa, said atraumatic body being configured to be located adjacent the second portion of the target when in said extended position; and
   an elongated measuring member coupled to said flexible filament, said elongated measuring member being a linear strip including a first portion located in said central passageway and a second portion extending out of said distal end centered on said central longitudinal axis when said atraumatic body is in said retracted position, said second portion including indicia thereon and being configured to be slid into said linear passageway along said central longitudinal axis in response to the movement of said atraumatic tip to said extended position, whereupon indicia located on said second portion of said elongated measuring member provides an indication of the distance between the first and second portions of the target.

2. The device of claim 1, wherein said elongated measuring member comprises a stop configured to prevent said elongated measuring member being pulled out of said distal end of said elongated tubular shaft.

3. The device of claim 1, additionally comprising a bushing located at said distal end of said elongated tubular shaft and including an opening through which said flexible filament extends.

4. The device of claim 1, wherein said atraumatic body is a ball.

5. The device of claim 1, wherein said elongated measuring member includes a proximal end extending out of said proximal end of said elongated tubular shaft and configured to be grasped by a user and pulled proximally to cause said atraumatic body to be in said retracted position.

6. The device of claim 1, wherein said indicia comprises a scale having regularly spaced marks extending along said second portion of said elongated measuring member.

7. The device of claim 1, wherein said elongated measuring member is resiliently-loaded to retract said atraumatic body to said retracted position.

8. The device of claim 7, wherein device additionally comprises an elongated resilient tension member connected between said distal end of said elongated tubular shaft and a portion of said elongated measuring member.

9. The device of claim 8, wherein said elongated resilient tension member comprises a tension spring.

10. The device of claim 8, wherein said device additionally comprises a pulley located adjacent said proximal end of said elongated tubular shaft, with a portion of said filament extending around said pulley.

* * * * *